(12) United States Patent
Britto et al.

(10) Patent No.: US 7,396,339 B2
(45) Date of Patent: Jul. 8, 2008

(54) PUMPING BREAST MILK

(75) Inventors: James J. Britto, Westport, MA (US); Shiu Hung Li, Taipo. N. T. (HK)

(73) Assignee: The First Years Inc., Avon, MA (US)

( * ) Notice: Subject to any disclaimer, the term of this patent is extended or adjusted under 35 U.S.C. 154(b) by 66 days.

(21) Appl. No.: 10/835,678

(22) Filed: Apr. 30, 2004

(65) Prior Publication Data

US 2005/0245860 A1 Nov. 3, 2005

(51) Int. Cl.
  *A61M 1/06* (2006.01)
  *A61M 1/00* (2006.01)
(52) U.S. Cl. .......................................... 604/74; 604/313
(58) Field of Classification Search ............. 604/73–76, 604/313–316
See application file for complete search history.

(56) References Cited

U.S. PATENT DOCUMENTS

| | | | |
|---|---|---|---|
| 3,238,937 A | 3/1966 | Stein | |
| 5,100,406 A * | 3/1992 | Panchula | 604/74 |
| 5,885,246 A * | 3/1999 | Ford | 604/74 |
| 5,947,923 A | 9/1999 | Uehara et al. | |
| 6,045,529 A | 4/2000 | Nuesch | |
| 6,139,521 A | 10/2000 | Larsson | |
| 6,257,847 B1 | 7/2001 | Silver et al. | |
| 6,355,012 B1 | 3/2002 | Nuesch | |
| 6,387,072 B1 * | 5/2002 | Larsson et al. | 604/74 |
| 6,461,324 B1 * | 10/2002 | Schlensog | 604/74 |
| 6,579,258 B1 * | 6/2003 | Atkin et al. | 604/74 |
| 6,663,587 B2 * | 12/2003 | Silver et al. | 604/74 |
| 6,673,036 B1 | 1/2004 | Britto | |
| 6,676,631 B1 | 1/2004 | Greter | |
| 6,964,651 B1 | 11/2005 | McKendry | |
| 2001/0038799 A1 | 11/2001 | Silver et al. | |
| 2002/0062103 A1 | 5/2002 | Larson et al. | |
| 2002/0072701 A1 | 6/2002 | Nuesch | |
| 2003/0069536 A1 | 4/2003 | Greter et al. | |
| 2005/0159701 A1 * | 7/2005 | Conaway | 604/74 |

* cited by examiner

*Primary Examiner*—Kevin C. Sirmons
*Assistant Examiner*—Andrew M Gilbert
(74) *Attorney, Agent, or Firm*—Michael Best & Friedrich LLP

(57) ABSTRACT

An apparatus for use in extracting milk from a human breast includes a pliant receiving member having an inner receiving portion sized to receive the human breast and an adjacent inner connecting portion defining an opening extending therethrough. The receiving member has an inner surface defining a recess located in the inner receiving portion and a passageway extending from the recess to the opening to provide fluid communication between the recess and the opening during use. The passageway provides fluid communication between the recess and the opening such that negative pressure can be generated between the recess and the breast.

44 Claims, 10 Drawing Sheets

PUMPING BREAST MILK

TECHNICAL FIELD

This invention relates to an apparatus for drawing milk from a human breast.

BACKGROUND

Many mothers rely on pumps to extract and store their breast milk. The more such pumps are automated and simulate the natural sucking rhythms of an infant, the easier it can be for a mother to relax and allow her milk to "let down" and flow. Devices have been proposed that stimulate the breast by generating negative pressure between opposing walls of a resilient insert adapted for receiving a human breast and a rigid funnel concentrically disposed about the insert.

SUMMARY

In an aspect, the invention features an apparatus for use in extracting milk from a human breast. The apparatus includes a pliant receiving member having an inner receiving portion sized to receive a human breast and an adjacent inner connecting portion defining an opening extending therethrough. The receiving member has an inner surface defining a recess located in the inner receiving portion and a passageway extending from the recess to the opening to provide fluid communication between the recess and the opening during use. The passageway provides fluid communication between the recess and the opening such that negative pressure can be generated between the recess and the breast.

In another aspect, the invention features an apparatus for use in extracting milk from a human breast. The apparatus features a pliant receiving member having an inner receiving portion sized to receive a human breast and an adjacent inner connecting portion defining an opening extending therethrough. The receiving member has an inner surface defining a recess located in the inner receiving portion and a raised rib extending outwardly from the inner surface within the recess.

In some embodiments, in response to the negative pressure generated between the recess and breast, the recess of the receiving member is configured to deform in a direction toward the breast and to recover upon removal of negative pressure. In some cases, the passageway is an open channel defined by the inner surface, the channel being configured to provide the passageway between the breast and the channel in use.

In many embodiments, the receiving portion of the receiving member is conical in shape and/or the connecting portion is tubular in shape. In certain cases, the connecting portion includes a throat of reduced inner diameter. In these cases, the passageway can extend from an end of the throat to the recess.

In some embodiments, the inner surface defines multiple, spaced-apart recesses located in the inner receiving portion and an associated passageway extending from each recess to the opening to provide fluid communication between the associated recess and the opening during use. In use, each passageway can provide fluid communication between the associated recess and the opening such that negative pressure can be generated between the associated recess and breast. In certain embodiments, in response to the negative pressure generated between the associated recess and breast, the associated recess of the receiving member is configured to deform in a direction toward the breast. In some embodiments, each passageway comprises an open channel defined by the inner surface, the channels being configured to provide the passageway between the breast and the channel in use. In certain embodiments, an outer surface of the receiving member defines an outer recess positioned between adjacent recesses defined by the inner surface. The outer surface of the receiving member can define multiple outer recesses, each outer recess positioned between adjacent recesses defined by the inner surface.

In some embodiments, a rigid outer member is connected to the receiving member where the outer member defines an outer opening through which the inner connecting portion of the receiving member extends. In many cases, the rigid outer member has an outer receiving portion sized and configured to receive the inner receiving portion of the receiving member. In some cases, the receiving member includes a peripheral passageway to inhibiting negative pressure from being generated between the outer and receiving members. The rigid outer member can include a tubular portion defining the outer opening through which the inner connecting portion of the receiving member extends. In some embodiments, the receiving member includes a ledge extending outwardly from an outer surface of the receiving member at the connecting portion. In some cases, an end surface of the receiving member at the connecting portion contacts the ledge to inhibit movement of the outer member relative to the receiving member during use.

In some embodiments, a raised rib extends outwardly from the inner surface of the receiving member within the recess. The rib can be configured to apply pressure to the breast during use. In some embodiments, the receiving member includes multiple raised ribs extending from the inner surface. Each of the raised ribs can be located within an associated recess.

In some embodiments, a conduit is permanently connected to the receiving member, or alternatively, the conduit can be releasably connected to the receiving member. A pump can be fluidly connected to the pliant receiving member.

In another aspect, the invention features a method of extracting milk from a breast. The method includes generating negative pressure between an inner surface of a pliant receiving member and a breast. The inner surface is sized to receive the breast and defines a recess located in an inner receiving portion. The recess formed by the inner surface is in fluid communication with a conduit connected to a pump. In response to negative pressure introduced between the inner surface and the breast, the pliant receiving member is deformed in a direction toward the breast.

In some embodiments, the step of deforming the pliant receiving member includes applying pressure to the breast. In some cases, pressure is applied by a raised rib located within the recess and extending from the inner surface. In certain embodiments, the receiving member is configured to recover to its original form upon removal of the negative pressure.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Referring to FIGS. 1A-1C, 3, 6A and 6B, an apparatus 10 suitable for use as part of a pump system includes a relatively rigid, funnel-shaped outer member 12 and a relatively pliant, funnel-shaped receiving member 14 concentric with the outer member 12. The receiving member 14 is constructed to deform in a direction toward a female's breast during use in response to negative pressure generated between the breast and the receiving member 14.

Figure 2:
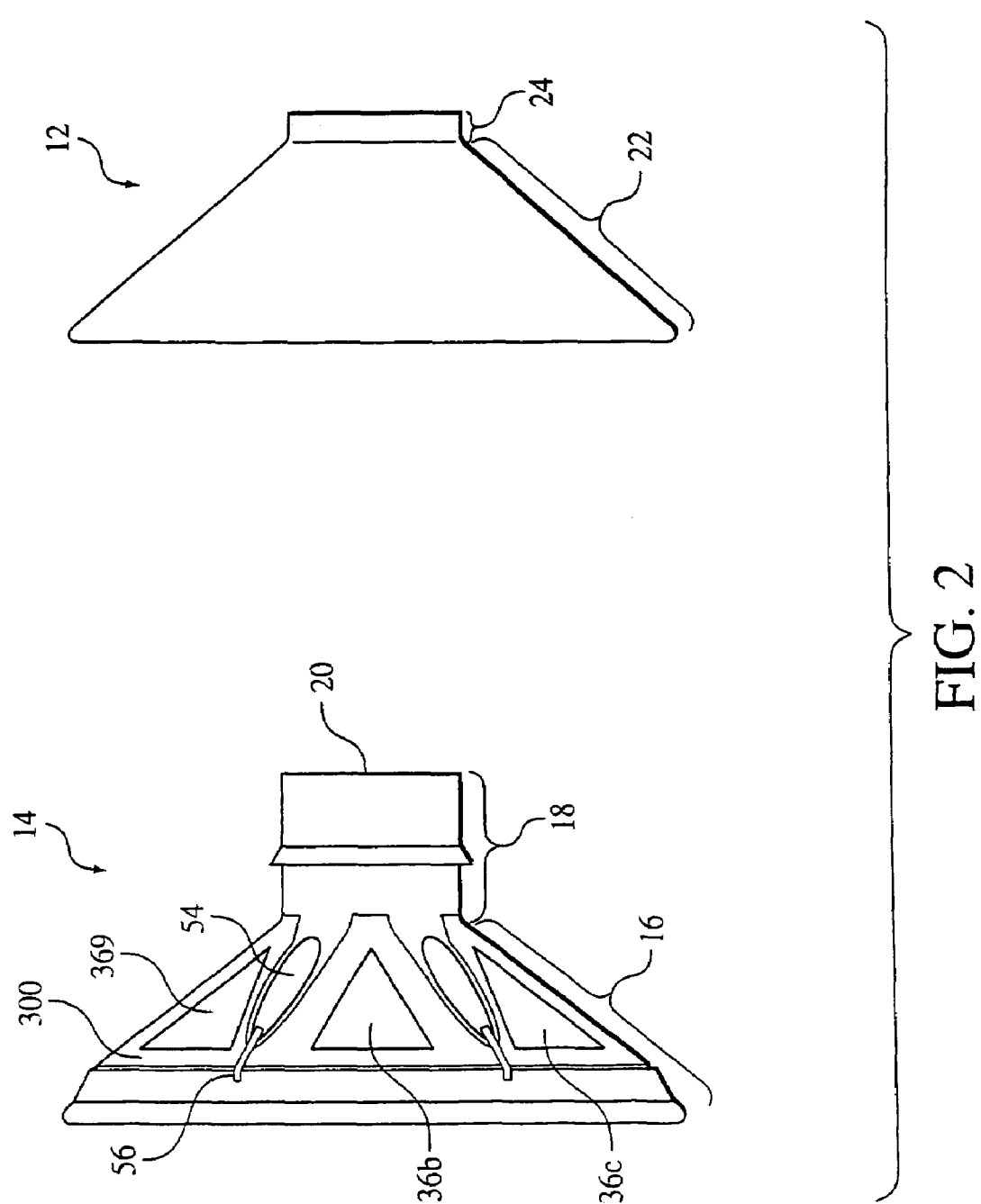
FIG. 2 is an exploded side view of the apparatus of FIG. 1A.

Referring now to FIG. 2, the receiving member 14 includes a conical receiving portion 16 that is sized to receive a human breast (see FIGS. 6A and 6B) and a tubular connecting portion 18 that can be, e.g., releasably connected to a pump. Extending through the connecting portion 18 is an opening 20 adapted for sealing engagement with a conduit (not shown). The outer member 12 includes a conical outer receiving portion 22 sized to receive the receiving portion 16 of the receiving member 14 and a tubular outer portion 24 having an outer opening 26 (FIG. 1B) that is sized to receive the connecting portion 18 of the receiving member 14.

Referring again to FIG. 1A, the receiving member 14 has a substantially smooth inner surface 28 and an array of equally-spaced, petal-shaped recesses 30a through 30f extending inwardly from the inner surface 28 that each provide a region of thinned wall thickness within the receiving portion 16 of the receiving member 14. The recesses 30, referring also to FIG. 1G, are gently contoured to provide comfort during use. Although six recesses 30 are shown, there can be more or less, such as from one to ten recesses, for example. Other recess shapes are also contemplated, such as pear-shapes, ovals, circles, polygons, etc. Located within each recess 30 is an associated messaging rib 32a through 32f of rounded cross-section (FIG. 1G) that protrudes outwardly from the inner surface 28. More than one messaging rib 32 can also be located within the recess 30. As will be described in greater detail, the messaging ribs 32 can apply pressure against a breast during use to stimulate the breast and facilitate lactation. The messaging ribs 32 can also position the breast within the receiving portion 16 of the receiving member 14 such that negative pressure can be generated between the breast and the inner surface 28.

Figure 1A:
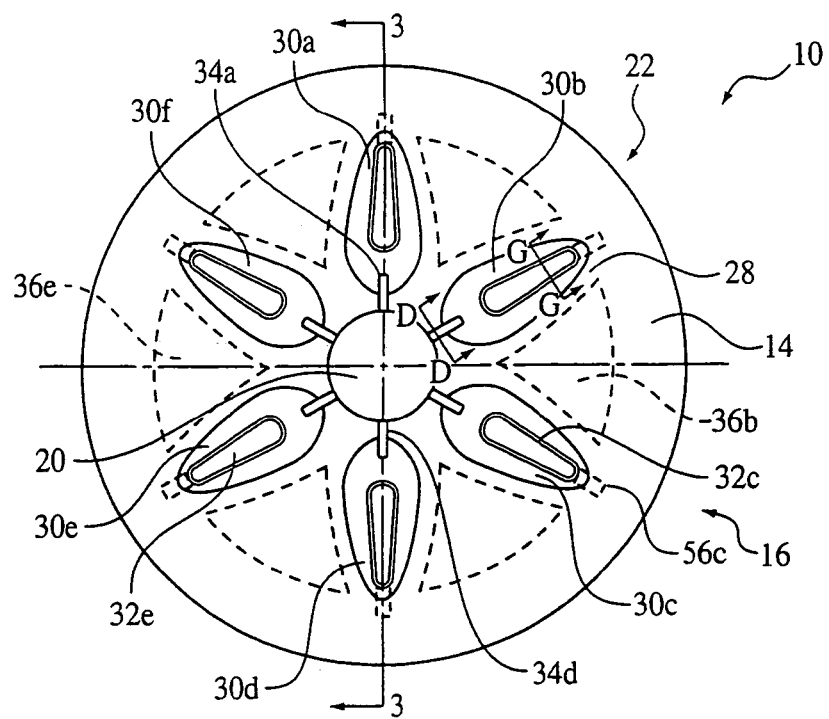
FIG. 1A is a top view of an embodiment of a pump apparatus.
Figure 1B:
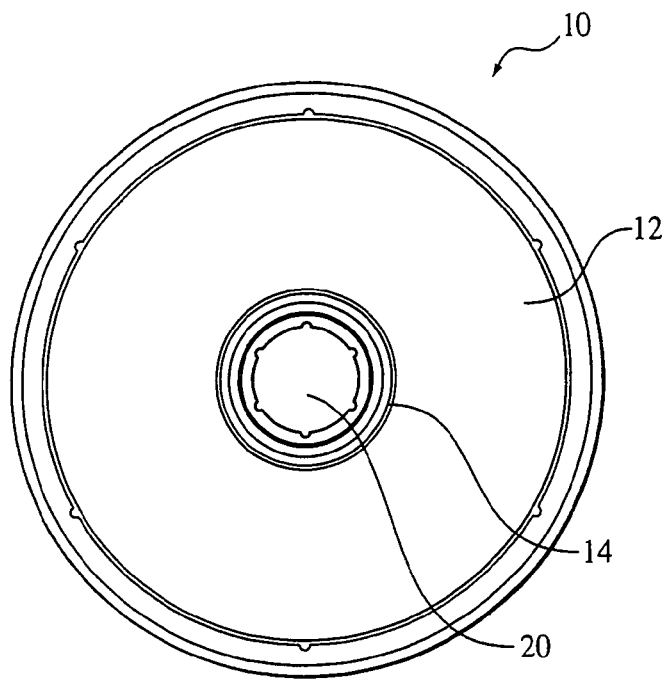
FIG. 1B is a bottom view of the pump apparatus of FIG. 1A.
Figure 1C:
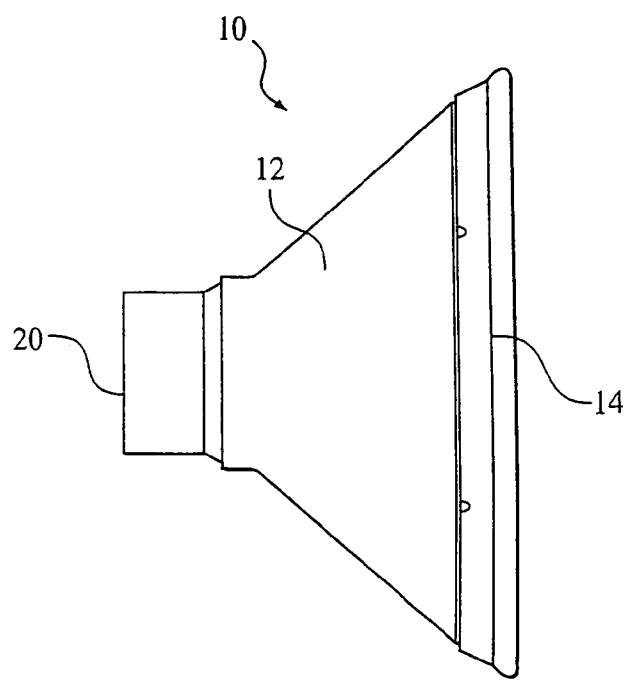
FIG. 1C is a side view of the pump apparatus of FIG. 1A.
Figure 1D:
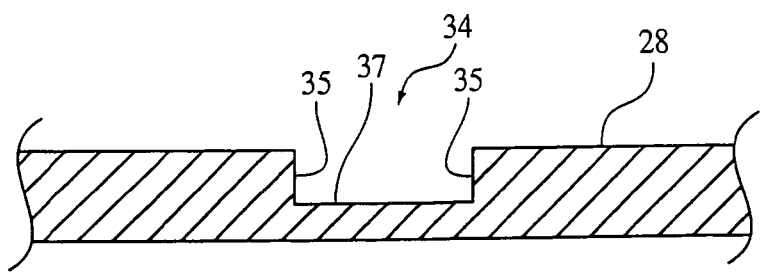
FIGS. 1D, 1E and 1F are section views of passageway examples along line D-D of FIG. 1A.
Figure 1E:
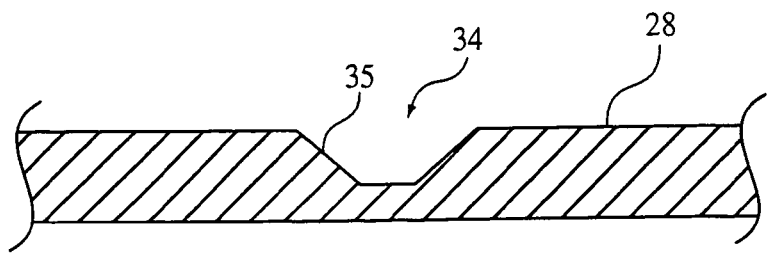
Figure 1F:
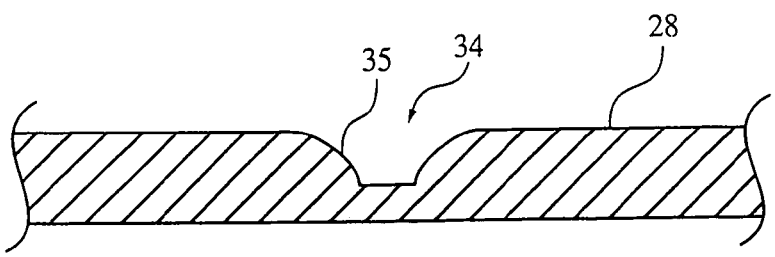
Figure 1G:
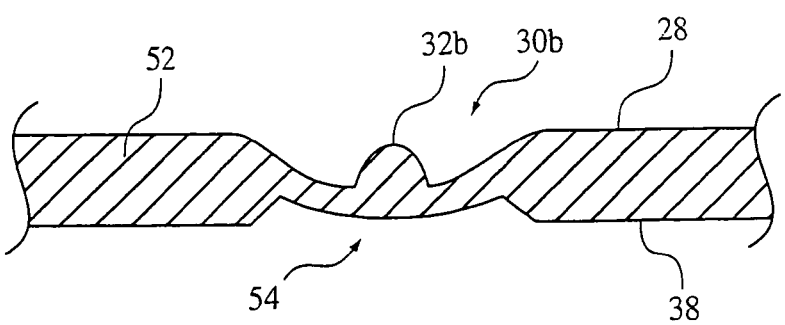
FIG. 1G is a section view of a recess and rib along line G-G of FIG. 1A.

Referring now to FIGS. 1A and 1D, beginning at each recess 30a through 30f and extending toward the opening 20 of the connecting portion 18 are passageways 34a through 34f. As shown, the passageways 34 are an open channel extending inwardly from the inner surface 28. The passageways 34 each include squared sidewalls 35 and a bottom surface 37. However, other configurations are contemplated. Referring to FIGS. 1E and 1F, the sidewalls 35 can be angled (FIG. 1E) or radiused (FIG. 1F). Also, the passageways 34 can be enclosed, such as an enclosed duct. The passageways 34 allow air to be drawn from each recess 30 during use such that negative pressure can be generated between the inner surface 28 and breast as will be described with reference to FIGS. 6A and 6B.

Referring also to FIG. 2, outer, triangle-shaped recesses 36 formed by an outer surface 38 of the receiving member 14 are located between adjacent recesses 30. The outer recesses 36 also form thinned wall regions extending inwardly from the outer surface 38 of the receiving member 14 that facilitate desired deformation of the receiving member 14 during use. The number of triangle-shaped recesses 36 can vary, e.g., depending on the number of recesses 30. In some embodiments, there are no triangle-shaped recesses 36.

Figure 3:
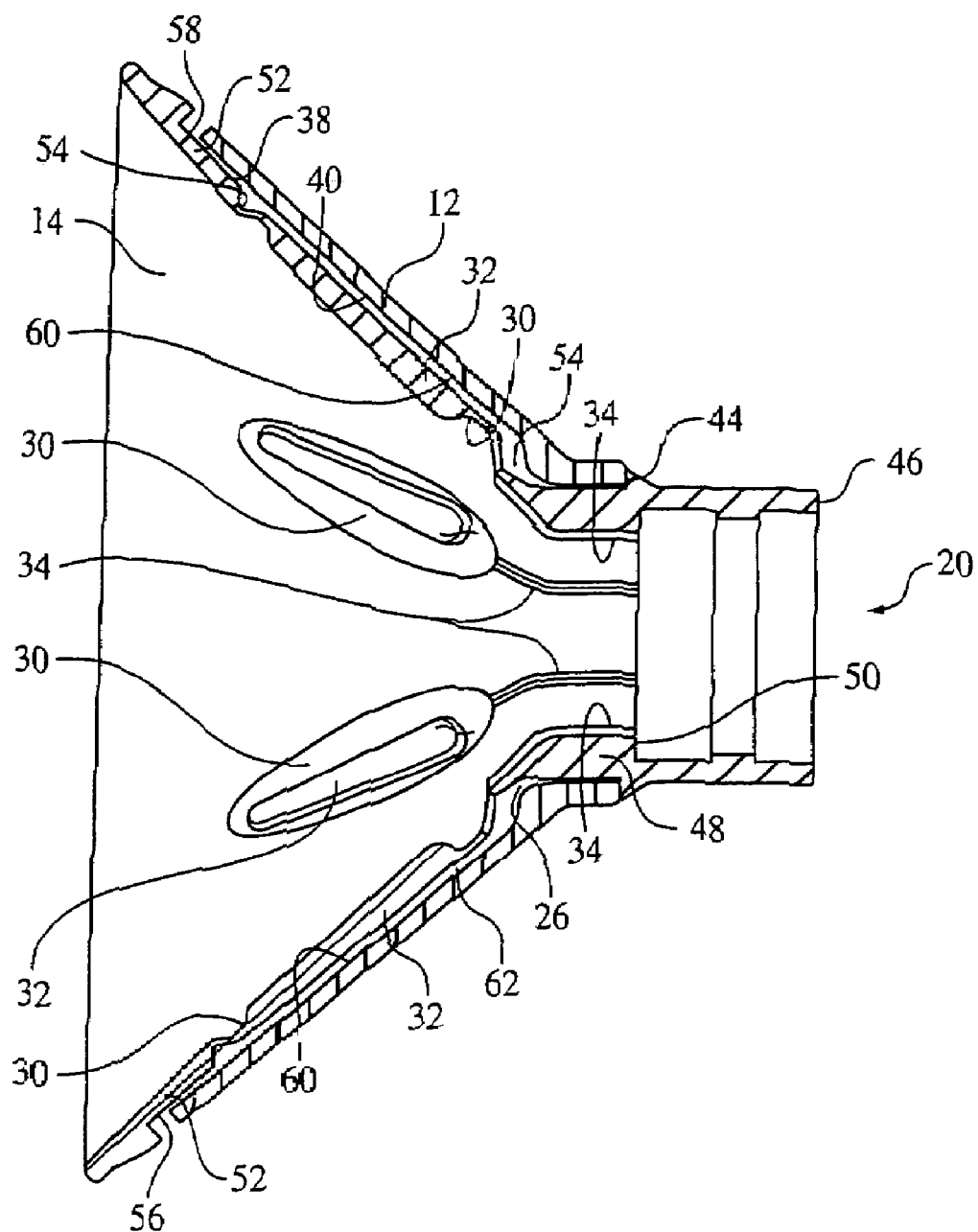
FIG. 3 is a section view of the pump apparatus of FIG. 1A along line 3-3.
Figure 4:
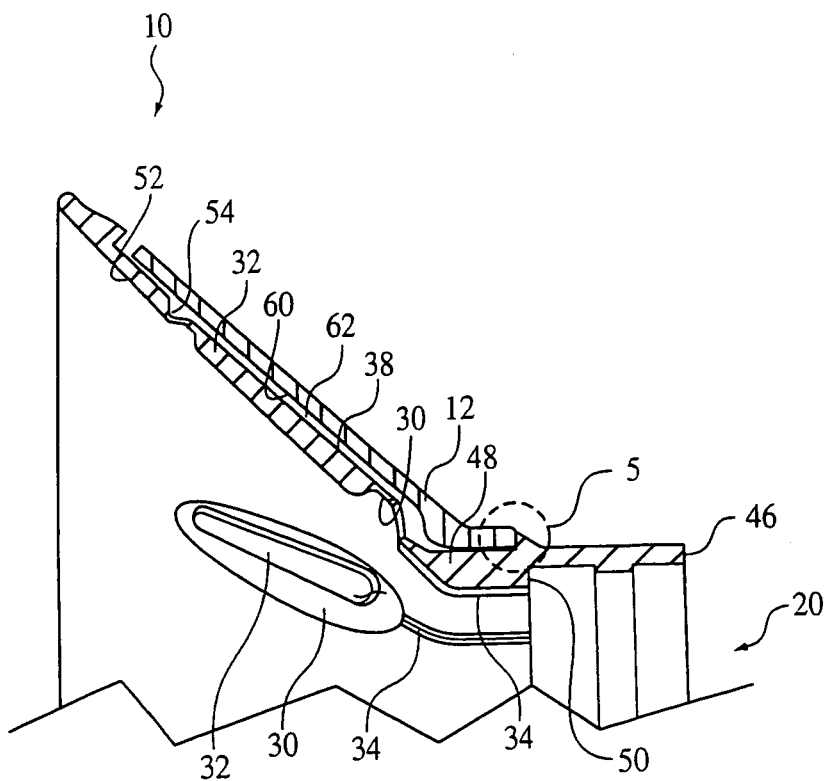
FIG. 4 is a section view of the pump apparatus of FIG. 1A in a deformed position.
Figure 5:
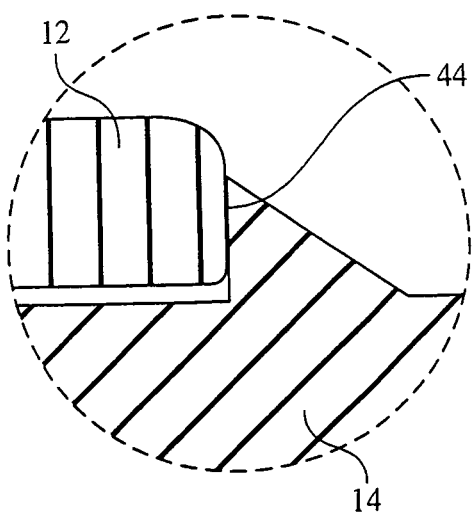
FIG. 5 is a detail view of engaging surfaces within area 5 of FIG. 4.

Referring now to FIGS. 3, 4 and 5, generally, the receiving member 14 is fitted within the rigid outer member 12 such that at least a portion of the outer surface 38 of the receiving member 14 opposes an inner surface 40 of the outer member 12. The outer member 12, as noted above, includes the conical outer receiving portion 22 terminating at the tubular outer portion 24 (FIG. 2). The tubular outer portion 24 is sized to be retained by a ledge 44 extending from the connecting portion 18 of the receiving member 14 when the connecting portion 18 is inserted through opening 26 of the outer member 12. The ledge 44 inhibits sliding of the outer and receiving members 12, 14 relative to each other during use.

Figure 6A:
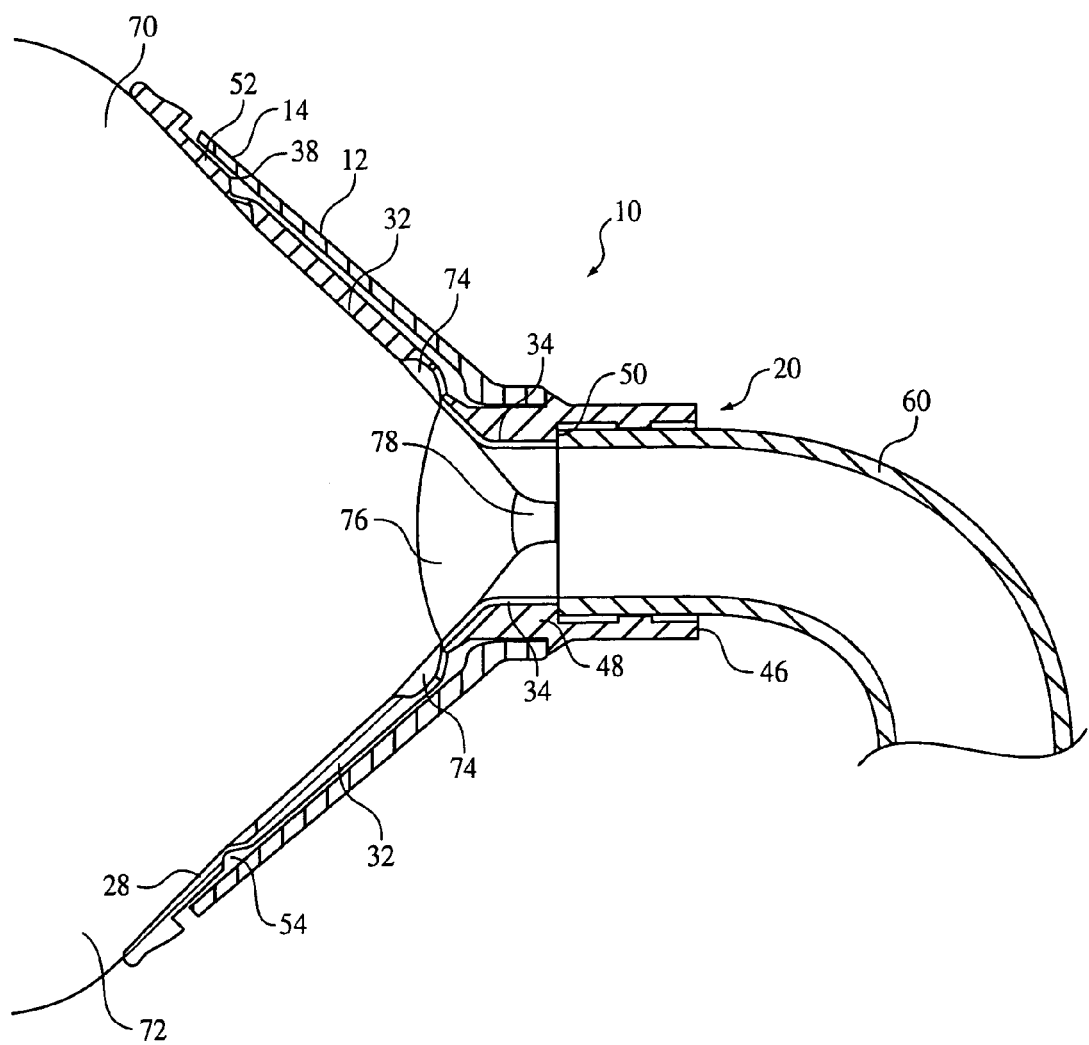
FIG. 6A is a section view of the pump apparatus of FIG. A in an undeformed, relaxed position during use.
Figure 6B:
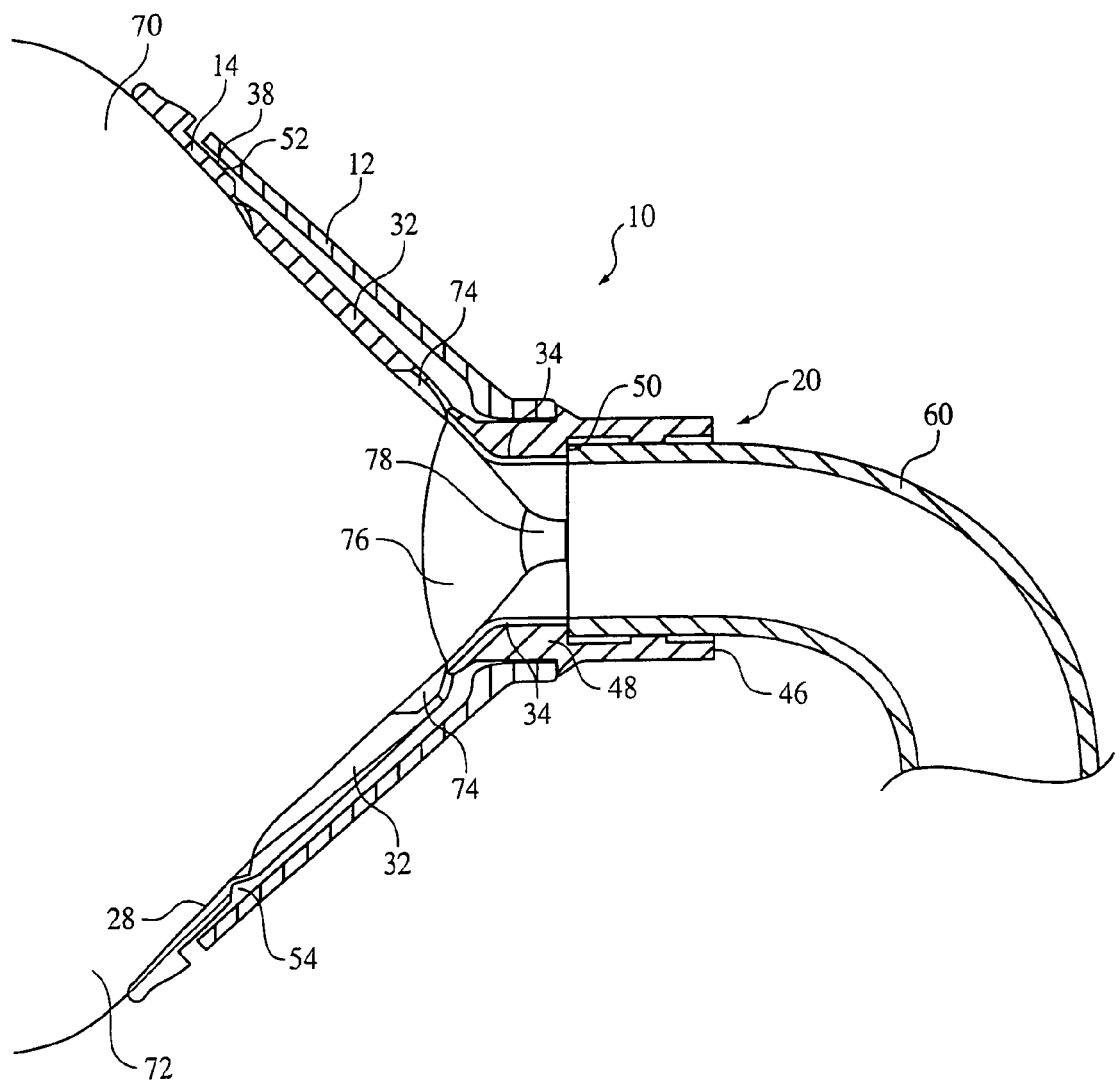
FIG. 6B is a section view of the pump apparatus of FIG. 1A in a deformed position during use.

Referring now to FIGS. 3, 4, 6A and 6B, the connecting portion 18 can be connected to a fluid conduit 60 (FIGS. 6A and 6B). The connection between the fluid conduit 60 can be permanent or separable. It is also contemplated that a conduit extends from the connecting portion 18 and can be connected to a pump. As shown, opening 20 of the tubular connecting portion 18 includes a terminal end 46 and a throat 48 that is spaced from the terminal end 46. The throat 48 has a reduced inner diameter relative to the inner diameter of the connecting portion 18 at the terminal end 46 to form an end, seating surface 50 for the fluid conduit, for example. Each of the passageways 34 extends from the associated recess 30a through 30f through throat 48 to the seating surface 50. In some embodiments, however, the passageways 34 (or only certain ones of the passageways 34) extend an intermediate distance and terminate at a location between the seating surface 50 and the recess 30. Importantly, the passageways are located to provide fluid communication with the recesses during use such that negative pressure can be generated between the recessed inner surface and the breast.

Referring also to FIGS. 1G, 2 and 3, wall 52 is relatively thin at the recess 30 adjacent the messaging rib 32, which facilitates deformation during use. As can be seen, the outer surface 38 is also recessed inwardly at regions 54 located opposite recesses 30a through 30f. Referring also to FIG. 1A, to further inhibit negative pressure from being generated between the receiving member and outer member 12 at regions 54, peripheral passageways 56 provide fluid communication between regions 54 and the atmosphere.

Referring now to FIGS. 3 and 4, the receiving member 14 is shown in its relaxed and flexed positions, respectively. Referring particularly to FIG. 3, in the relaxed position, the ribs 32 and surrounding areas are relatively near an inner surface 60 of the outer member 12. When negative pressure is generated between the breast and the receiving member 14, as shown in FIG. 3, the receiving member deforms in a radially inward direction away from surface 60 and toward the breast increasing a gap 62 between the outer member 12 and the receiving member 14.

Suitable materials for forming the outer member 12 can include polymers, such as polypropylene (PP), polystyrene (PS), acrylonitrile-butadiene-styrene (ABS), polycarbonate (PC) and KRYLON®. Suitable materials for forming the receiving member 14 can include rubber, such as latex, polymers, such as silicone, thermoplastic elastomers, polyvinyl chloride (PVC) and ethylene-vinyl acetate (EVA). Additionally, any suitable method can be employed for forming the outer and receiving members including machining, molding, such as injection molding, compression molding and vacuum forming.

Referring now to FIGS. 6A and 6B, apparatus 10 is shown in use with breast 70 received by the receiving member 14. The apparatus 10 is connected to conduit 60 that is inserted into opening 20 and seated against seating surface 50. The conduit 60 is connected to a pump (not shown) that is capable of generating negative pressure. Outer surface 72 of the breast 70 seats against the inner surface 28 of the receiving member 14 forming chambers 74 between the breast 70 and the recesses 30a through 30f. The outer member 12 and the messaging ribs 32 about the outer surface 72 of the breast 70 serve as support structures to help form the chambers 74 by positioning the outer surface 72 spaced from the recesses 30. The passageways 34 extending from the recesses to the seating surface 50 allow for fluid communication between each of the chambers 74 and the conduit 60.

Referring to FIG. 6A, prior to activating the pump, the receiving member 14 is in a relaxed, undeformed position, applying relatively light pressure against the breast 70. Referring now to FIG. 6B, when the pump is activated, negative pressure is generated within at least chambers 74 via the passageways 34. Due to the negative pressure (e.g., between about 25 mmHG and 380 mmHG, preferably between about 50 mmHG and 280 mmHG), the receiving member 14 deforms in a direction toward the breast 70 and messaging ribs 32 apply localized pressure to create a massaging effect to stimulate milk let down. On release of negative pressure, the receiving member 14 recovers toward its initial, relaxed position to reduce the amount of pressure applied to the breast. Typically, the pump automatically cycles vacuum pressure and deforms the receiving member 14 to simulate the natural sucking rhythms of an infant. Milk extracted from the breast flows from the apparatus 10 into a removable storage bottle or receptacle 106 (FIG. 7), for example, attached to the fluid conduit 60.

While the messaging ribs 32 are shown in FIGS. 6A and 6B contacting surface 72 at a location spaced from the areola 76 and nipple 78, other configurations are contemplated. For example, the ribs 32 can be constructed to contact the areola 76 and/or the nipple 78 to encourage milk let-down. In some embodiments, the ribs 32 contact only the areola 76. Additionally, the size and/or shape of the apparatus can be selected to accommodate a particular breast size.

Figure 7:
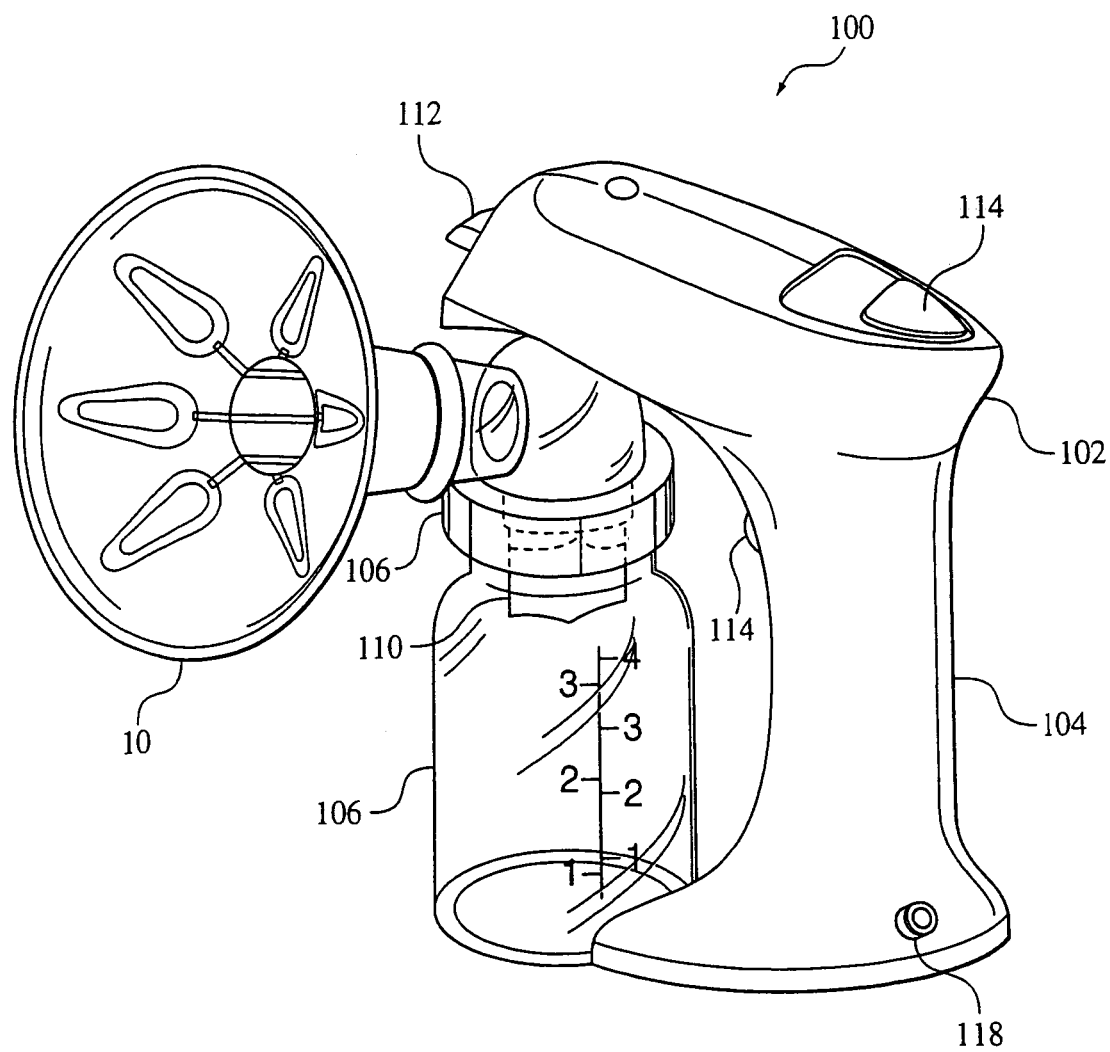
FIG. 7 is a perspective view of an embodiment of a pump device including the pump apparatus of FIG. 11A.

Referring now to FIG. 7, an exemplary pump system 100 for use with apparatus 10 includes a main body 102 that forms a graspable handle 104 for holding the pump with one hand during operation. Bottle 106 is connected to body 102 and apparatus 10 by a 3-way adaptor or vacuum bulkhead 108, through which milk flows from apparatus 10 to bottle 106 through a valve cup 110. The bottle and hood are suspended from pump body 102 by bulkhead 108, which is released from body 102 by depressing a release plunger 112. The only two user operation controls provided on the pump are an on/off button 114 and a vacuum level adjustment dial 116, which is located on handle 104 for convenient manipulation during operation. Pump 100 is battery-operated, and a power jack 118 at the base of the pump is provided for connecting the pump to household current through a typical AC/DC converter (not shown). A suitable pump example is described in U.S. Pat. No. 6,673,036, the entire contents of which are hereby incorporated by reference.

Figure 8:
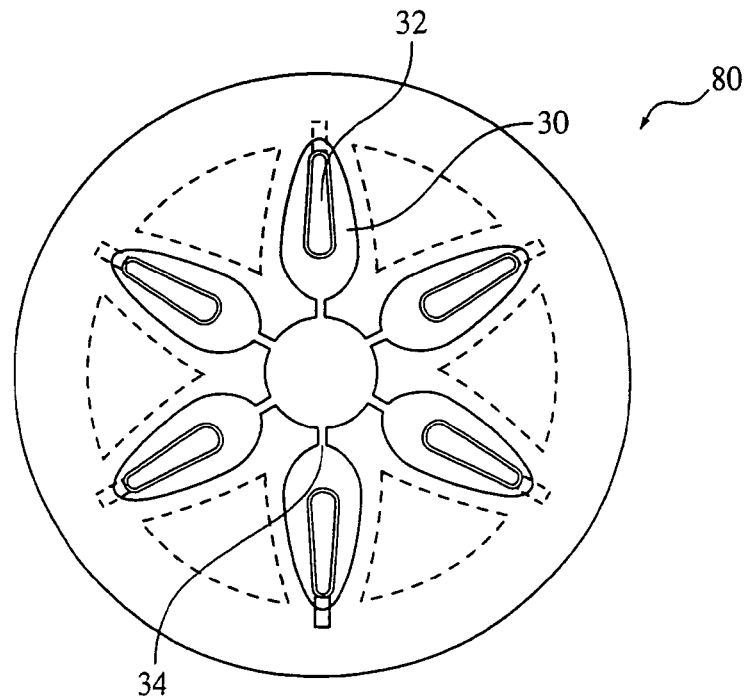
FIG. 8 is another embodiment of a pump apparatus.
Figure 9A:
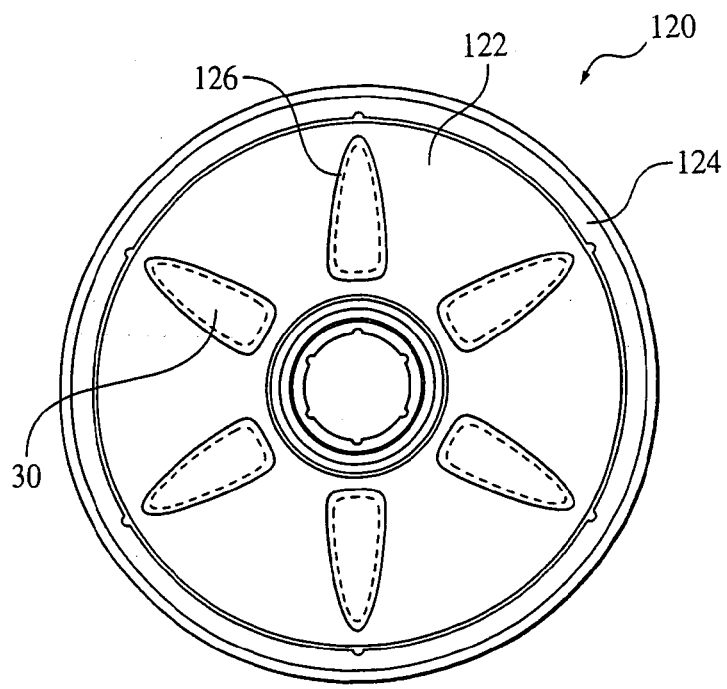
FIG. 9A is a top view of another embodiment of a pump apparatus.
Figure 9B:
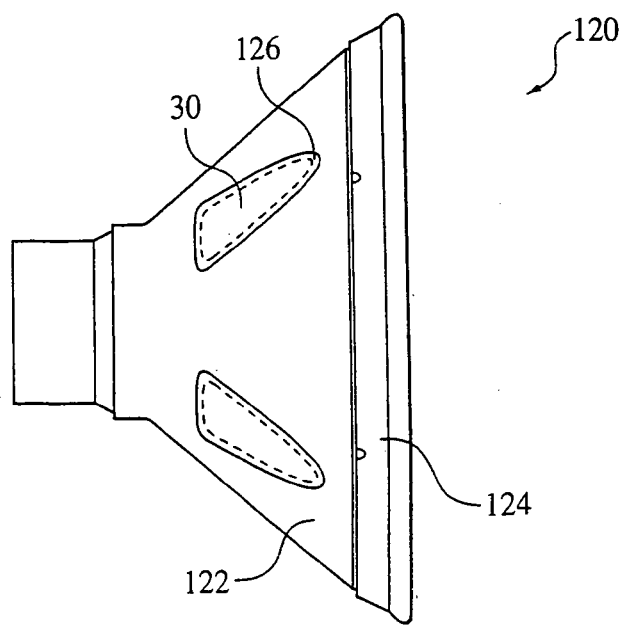
FIG. 9B is a plan view of another embodiment of a pump apparatus.

A number of embodiments of the invention have been described. Nevertheless, it will be understood that various modifications may be made without departing from the spirit and scope of the invention. For example, referring to FIG. 8, another apparatus 80 is shown where the recesses 30 extends inward to form the passageways 34. As another example, referring to FIGS. 9A and 9B, an apparatus 120 includes a pliant receiving member 124 and a rigid outer member 122 integrally connected to the receiving member 124 (e.g., by overmolding the outer and receiving members). The outer member 122 includes an array of openings 126 extending through the wall 128 at the receiving portion of the outer member 122. Each opening 126 is aligned with a recess 30 (shown in phantom) of the receiving member 124. The openings 126 allow the recesses 30 to deflect when negative pressure is generated between the recess 30 and breast, as described above. Accordingly, other embodiments are within the scope of the following claims.

What is claimed is:

1. An apparatus for use in extracting milk from a human breast, the apparatus comprising:
   a pliant receiving member having an inner receiving portion sized to receive a human breast and an adjacent inner connecting portion defining an opening extending therethrough, the receiving member having an inner surface adapted to contact at least a portion of the human breast, the inner surface including a recess located in the inner receiving portion and a passageway having a length extending from the recess to the opening to provide fluid communication between the recess and the opening during use;
   wherein the passageway includes a width smaller than a width of the recess along its length, and provides fluid communication between the recess and the opening such that negative pressure can be developed within the recess at the breast;
   a rigid outer member connected to the receiving member, the outer member defining an outer opening through which the inner connecting portion of the receiving member extends;
   wherein the rigid outer member has an outer receiving portion sized and configured to receive the inner receiving portion of the receiving member; and
   wherein the receiving member includes a peripheral passageway to inhibit negative pressure from being generated between the outer member and the receiving member.

2. The apparatus of claim 1, wherein, in response to the negative pressure generated between the recess and breast, the recess of the receiving member is configured to deform in a direction toward the breast and to recover upon removal of negative pressure.

3. The apparatus of claim 1, wherein the passageway comprises an open channel defined by the inner surface, the channel being configured to provide the passageway between the breast and the channel in use.

4. The apparatus of claim 1, wherein the receiving portion of the receiving member is conical in shape.

5. The apparatus of claim 4, wherein the connecting portion is tubular in shape.

6. The apparatus of claim 5, wherein the connecting portion includes a throat of reduced inner diameter.

7. The apparatus of claim 6, wherein the passageway extends from an end of the throat to the recess.

8. The apparatus of claim 1, wherein the inner surface defines multiple, spaced-apart recesses located in the inner receiving portion and an associated passageway extending from each recess to the opening to provide fluid communication between the associated recess and the opening during use.

9. The apparatus of claim 8, wherein, in use, each passageway provides fluid communication between the associated recess and the opening such that negative pressure can be generated between the associated recess and breast.

10. The apparatus of claim 9, wherein, in response to the negative pressure generated between the associated recess and breast, the associated recess of the receiving member is configured to deform in a direction toward the breast.

11. The apparatus of claim 8, wherein each passageway comprises an open channel defined by the inner surface, the channels being configured to provide the passageway between the breast and the channel in use.

12. The apparatus of claim 8, wherein an outer surface of the receiving member defines an outer recess positioned between adjacent recesses defined by the inner surface.

13. The apparatus of claim 12, wherein the outer surface of the receiving member defines multiple outer recesses, each outer recess positioned between adjacent recesses defined by the inner surface.

14. The apparatus of claim 1, wherein the rigid outer member includes a tubular portion defining the outer opening through which the inner connecting portion of the receiving member extends.

15. The apparatus of claim 14 comprising a ledge extending outwardly from an outer surface of the receiving member at the connecting portion.

16. The apparatus of claim 15, wherein an end surface of the outer member at the tubular portion contacts the ledge to inhibit movement of the outer member relative to the receiving member during use.

17. The apparatus of claim 1 further comprising a conduit permanently connected to the receiving member.

18. The apparatus of claim 1 further comprising a conduit releasably connected to the receiving member.

19. The apparatus of claim 1 further comprising a pump fluidly connected to the pliant receiving member.

20. An apparatus for use in extracting milk from a human breast, the apparatus comprising:
a pliant receiving member having an inner receiving portion sized to receive a human breast and an adjacent inner connecting portion defining an opening extending therethrough, the receiving member having an inner surface defining a recess located in the inner receiving portion and a raised rib extending outwardly from the inner surface within the recess;
the receiving member having a wall thickness in the recess that is relatively thinner around the rib than in a region of the receiving member surrounding the recess.

21. The apparatus of claim 20, wherein the rib is configured to apply pressure to the breast during use.

22. The apparatus of claim 20, wherein the inner surface defines a passageway extending from the recess to the opening to provide fluid communication between the recess and the opening during use.

23. The apparatus of claim 22, wherein, in use, the passageway provides fluid communication between the recess and the opening such that negative pressure can be generated between the recess and breast.

24. The apparatus of claim 23, wherein, in response to the negative pressure generated between the recess and breast, the recess of the receiving member is configured to deform in a direction toward the breast.

25. The apparatus of claim 22, wherein the passageway comprises an open channel defined by the inner surface, the channel being configured to provide the passageway between the breast and the channel in use.

26. The apparatus of claim 20, wherein the inner surface defines multiple, spaced-apart recesses located in the inner receiving portion.

27. The apparatus of claim 26, wherein the receiving member includes multiple raised ribs extending from the inner surface.

28. The apparatus of claim 27, wherein each raised rib is located within an associated recess.

29. The apparatus of claim 26, wherein the inner surface of the receiving member defines associated passageways extending from a respective recess to the opening to provide fluid communication between the associated recess and the opening during use.

30. The apparatus of claim 29, wherein, in use, each passageway provides fluid communication between the associated recess and the opening such that negative pressure can be generated between the associated recess and breast.

31. The apparatus of claim 30, wherein, in response to the negative pressure generated between the associated recess and breast, the associated recess of the receiving member is configured to deform in a direction toward the breast.

32. The apparatus of claim 30, wherein each passageway comprises an open channel defined by the inner surface, the channels being configured to provide the passageway between the breast and the channel in use.

33. The apparatus of claim 26, wherein an outer surface of the receiving member defines an outer recess positioned between adjacent recesses defined by the inner surface.

34. The apparatus of claim 33, wherein the outer surface of the receiving member defines multiple outer recesses, each outer recess positioned between adjacent recesses defined by the inner surface.

35. The apparatus of claim 20 further comprising a rigid outer member connected to the receiving member, the outer member defining an outer opening through which the inner connecting portion of the receiving member extends.

36. The apparatus of claim 35, wherein the rigid outer member has an outer receiving portion sized and configured to receive the inner receiving portion of the receiving member.

37. The apparatus of claim 35, wherein the rigid outer member includes a cylindrical portion defining the outer opening through which the inner connecting portion of the receiving member extends.

38. The apparatus of claim 35 comprising a ledge extending outwardly from an outer surface of the receiving member at the connecting portion.

39. The apparatus of claim 38, wherein an end surface of the outer member at the cylindrical portion contacts the ledge to inhibit movement of the outer member relative to the receiving member.

40. The apparatus of claim 20 further comprising a conduit permanently connected to the receiving member.

41. The apparatus of claim 20 further comprising a conduit releasably connected to the receiving member.

42. The apparatus of claim 20 further comprising a pump fluidly connected to the pliant receiving member.

43. The apparatus of claim 20, wherein the receiving portion of the receiving member is conical in shape.

44. The apparatus of claim 43, wherein the connecting portion is cylindrical in shape.

* * * * *